United States Patent
Yoshinari et al.

(10) Patent No.: US 10,229,821 B2
(45) Date of Patent: Mar. 12, 2019

(54) MASS SPECTROMETRY DEVICE

(71) Applicant: Hitachi High-Technologies Corporation, Minato-ku, Tokyo (JP)

(72) Inventors: Kiyomi Yoshinari, Tokyo (JP); Yasushi Terui, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 15/542,505

(22) PCT Filed: Jan. 4, 2016

(86) PCT No.: PCT/JP2016/050002
§ 371 (c)(1),
(2) Date: Jul. 10, 2017

(87) PCT Pub. No.: WO2016/114151
PCT Pub. Date: Jul. 21, 2016

(65) Prior Publication Data
US 2018/0269049 A1    Sep. 20, 2018

(30) Foreign Application Priority Data
Jan. 15, 2015 (JP) .................. 2015-005481

(51) Int. Cl.
 *H01J 49/00* (2006.01)
 *G01N 27/62* (2006.01)
 *H01J 49/42* (2006.01)
(52) U.S. Cl.
 CPC .......... *H01J 49/0063* (2013.01); *G01N 27/62* (2013.01); *H01J 49/4215* (2013.01); *H01J 49/4255* (2013.01)
(58) Field of Classification Search
 CPC ............... H01J 49/0063; H01J 49/4215; H01J 49/4255; G01N 27/62
(Continued)

(56) References Cited

U.S. PATENT DOCUMENTS 6,060,705 A * 5/2000 Whitehouse .......... H01J 49/165
                                                                250/281
2003/0189168 A1   10/2003 Londry et al.
(Continued)

FOREIGN PATENT DOCUMENTS

JP    2005-522845 A    7/2005
JP    2007-171200 A    7/2007
(Continued)

OTHER PUBLICATIONS

International Search Report (PCT/ISA/210) issued in PCT Application No. PCT/JP2016/050002 dated Mar. 29, 2016 with English translation (six pages).
(Continued)

*Primary Examiner* — Nicole Ippolito
(74) *Attorney, Agent, or Firm* — Crowell & Moring LLP

(57) ABSTRACT

With regard to an object of the invention, in a tandem type mass spectrometry system including three stages of a QMS, sensitivity of a daughter ion decreases due to loss resulting from destabilization of the daughter ion or a decrease in daughter ion generation rate, and an improvement insensitivity of the daughter ion is a significant issue. To solve the above-mentioned problem, the invention provides a mass spectrometry system having means of decreasing a q value of a parent ion and not decreasing a fundamental vibration frequency of the parent ion. According to the means of the invention, the invention may have effects that a mass number range of a daughter ion that may be stably transmitted is expanded, the number of vibrations of a parent ion is substantially the same as that in a first stage of the QMS, and generation efficiency of the daughter ion does not decrease and can be maintained.

12 Claims, 8 Drawing Sheets

(58) Field of Classification Search
USPC ........................................ 250/281, 282, 283
See application file for complete search history.

(56) References Cited

U.S. PATENT DOCUMENTS

| | | |
|---|---|---|
| 2007/0145264 A1 | 6/2007 | Specht et al. |
| 2009/0179148 A1* | 7/2009 | Yasuda ................ H01J 49/004 250/282 |
| 2009/0194683 A1 | 8/2009 | Guna et al. |
| 2009/0194684 A1 | 8/2009 | Guna et al. |
| 2010/0059675 A1* | 3/2010 | Mukaibatake ........ H01J 49/065 250/288 |
| 2012/0032074 A1 | 2/2012 | Kenny |
| 2012/0292498 A1* | 11/2012 | Jiang .................... H01J 49/004 250/282 |

FOREIGN PATENT DOCUMENTS

| | | |
|---|---|---|
| JP | 2011-511274 A | 4/2011 |
| JP | 2011-511401 A | 4/2011 |
| JP | 2012-516013 A | 7/2012 |

OTHER PUBLICATIONS

Japanese-language Written Opinion (PCT/ISA/237) issued in PCT Application No. PCT/JP2016/050002 dated Mar. 29, 2016 (three pages).

* cited by examiner

MASS SPECTROMETRY DEVICE

TECHNICAL FIELD

The present invention relates to a mass spectrometry device using a tandem type quadrupole mass spectrometer, and particularly relates to a mass spectrometry device that requires high sensitivity in a case of analytical use for an in vivo sample, and the like.

BACKGROUND ART

In a quadrupole mass spectrometer (QMS) including at least four rod-like electrodes to which a direct current voltage U and a high frequency voltage $V \cos(\Omega t+\Phi_0)$ are applied, stability of an ion trajectory passing through a high frequency electric field generated among the electrodes is determined in a stable transmission area based on stability parameter values a and q illustrated in FIG. 3. The stability parameters a and q are expressed by the following Equations.

[Equation 1]
$$a = \frac{8eZU}{\Omega^2 m r_0^2} \qquad (1)$$

[Equation 2]
$$q = \frac{4eZV}{\Omega^2 m r_0^2} \qquad (2)$$

Here, a mass-to-charge ratio of a target ion is m/Z, $r_0$ denotes a half value of a distance between rod-like electrodes facing each other, e denotes an elementary charge, U denotes a direct current voltage, and V and $\Omega$ denote an amplitude and an angular vibration frequency of a high frequency voltage.

Conventionally, in a tandem type mass spectrometry device including three stages of the QMS, in a first stage of the QMS (Q1), only an ion species having a specific mass-to-charge ratio m/z passes through Q1, and thus a voltage applied to an electrode is adjusted such that an operating point corresponds to a point near an apex of the stable transmission area as illustrated in FIG. 4a. In a second stage of the QMS (Q2), a specific ion species (parent ion) passing through Q1 is broken by collision induced dissociation, or the like to generate a dissociated ion (daughter ion). In this instance, in order to stably pass a daughter ion in a wide mass number range, the direct current voltage is set to U=0 and the same voltage $V \cos(\Omega t+\Phi_0)$ as that in Q1 is applied as the high frequency voltage among the voltages applied to the electrodes in Q2 such that the operating point is on an a=0 axis, and the q value is the same between Q1 and Q2 as illustrated in FIG. 4a.

In addition, as described in JP 2012-516013 A, in the second stage of the QMS (Q2), the direct current voltage is set to U=0, the amplitude of the high frequency voltage $V \cos(\Omega t+\Phi_0)$ is the same as that in the case of Q1, and a frequency $\Omega/(2\pi)$ is set to be larger than or smaller than a frequency in Q1.

CITATION LIST

Patent Literature

PTL 1: JP 2012-516013 A

SUMMARY OF INVENTION

Technical Problem

In a tandem type mass spectrometry device including three stages of the QMS, a mass of a parent ion is selected and separated in a first stage of the QMS (Q1), the parent ion is dissociated to generate and stably transmit a daughter ion in a second stage of the QMS (Q2), and mass spectrum analysis is performed on various daughter ions in a third stage of the QMS (Q3).

Conventionally, as illustrated in FIG. 4a, in Q1, only an ion species having a specific mass-to-charge ratio m/z passes through Q1, and thus a voltage applied to an electrode is adjusted such that an operating point corresponds to a point near an apex of the stable transmission area. In Q2, in order to stably pass a daughter ion generated by breaking a parent ion passing through Q1, only a direct current voltage is changed to U=0, and a high frequency voltage is not changed such that an operating point is on an a=0 axis. In this instance, as illustrated in FIG. 4a, since a value of a stability parameter q of the parent ion is almost unchanged, the daughter ion generated by dissociating the parent ion has a lower mass number than that of the parent ion, and thus m/Z becomes smaller. As a result, as illustrated in Equation (2), a q value of the daughter ion is larger than a q value of the parent ion, some daughter ions come out of the stable area, and there is a possibility that stable transmission (detection) will not be allowed, and sensitivity will decrease.

In addition, as described in JP 2012-516013 A, in the second stage of the QMS (Q2), when the direct current voltage is set to U=0, and the amplitude V is the same as that in the case of Q1 and the frequency $\Omega/(2\pi)$ is larger than the frequency of Q1 with regard to the high frequency voltage $V \cos(\Omega t+\Phi_0)$, the q value of the parent ion decreases, and the q value of the daughter ion decreases as illustrated in FIG. 4b, and thus a mass number range of a daughter ion that may be stably transmitted increases. However, when the q value of the parent ion is merely decreased, a fundamental vibration frequency (Equation (3)) of the parent ion decreases as illustrated in FIG. 5a.

[Equation 3]
$$\omega \approx \frac{q\Omega}{2\sqrt{2}} = \frac{\sqrt{2}\, eZV}{m r_0^2 \Omega} \qquad (3)$$

In this instance, when the fundamental vibration frequency of the parent ion decreases, in particular, when the parent ion is dissociated by a CID, the number of collisions with buffer gas such as neutral gas decreases. Therefore, since dissociation efficiency of the parent ion, that is, a generation rate of the daughter ion is reduced, there is a possibility that sensitivity of the daughter ion may be reduced.

That is, in the conventional method, two problems below are considered.

(1) Decrease in sensitivity due to an unstable trajectory of the daughter ion (coming out of the stable area)

(2) Decrease in sensitivity due to a decrease in generation efficiency of the daughter ion (a decrease in the number of vibrations of the parent ion)

To solve the above-described problems, means of not decreasing the fundamental vibration frequency of the parent ion while decreasing the q value of the parent ion is required.

Solution to Problem

In the invention, in a tandem type quadrupole mass spectrometry system, as means of not decreasing a fundamental vibration frequency of a parent ion while decreasing a q value of the parent ion in order to solve the above-described problems, when a q value of the parent ion in Q1 is set to q1, a q value of the parent ion in Q2 is set to q2, and fundamental vibration frequencies of the parent ion in Q1 and Q2 are set to ω1 and ω2,

[Equation 4]
$$q_2 = \frac{1}{\gamma} q_1 \; (Y > 1) \quad (4)$$

[Equation 5]
$$\omega_2 = \omega_1 \quad (5)$$

[Equation 6]
$$\Omega_2 = \gamma \cdot \Omega_1 (Y > 1) \quad (6)$$

Here, in order to satisfy both Equations (4) and (5), Equation (6) needs to be satisfied. Therefore, in order to satisfy Equations (4) to (6), applied voltages (a direct current voltage U and a high frequency voltage V cos(Ωt)) of Q1 and Q2 are controlled, and a distance between electrodes of Q1 and Q2 is changed such that the following Equation is satisfied.

[Equation 7]
$$\frac{V_1}{r_{0_1}^2 \Omega_1} = \frac{V_2}{r_{0_2}^2 \Omega_2} (\Omega_1 \neq \Omega_2) \quad (7)$$

Effects that a mass number range of a daughter ion that may be stably transmitted is expanded and generation efficiency of the daughter ion does not decrease (the number of vibrations of the parent ion is substantially the same as that in Q1) are considered to be expectable by the means of the invention.

Advantageous Effects of Invention

As described above, effects that a mass number range of a daughter ion that may be stably transmitted is expanded and generation efficiency of the daughter ion does not decrease (the number of vibrations of the parent ion is substantially the same as that in Q1) are considered to be expectable in a tandem type quadrupole mass spectrometry system of the invention.

DESCRIPTION OF EMBODIMENTS

Hereinafter, embodiments of the invention will be described with reference to drawings.

Figure 1:
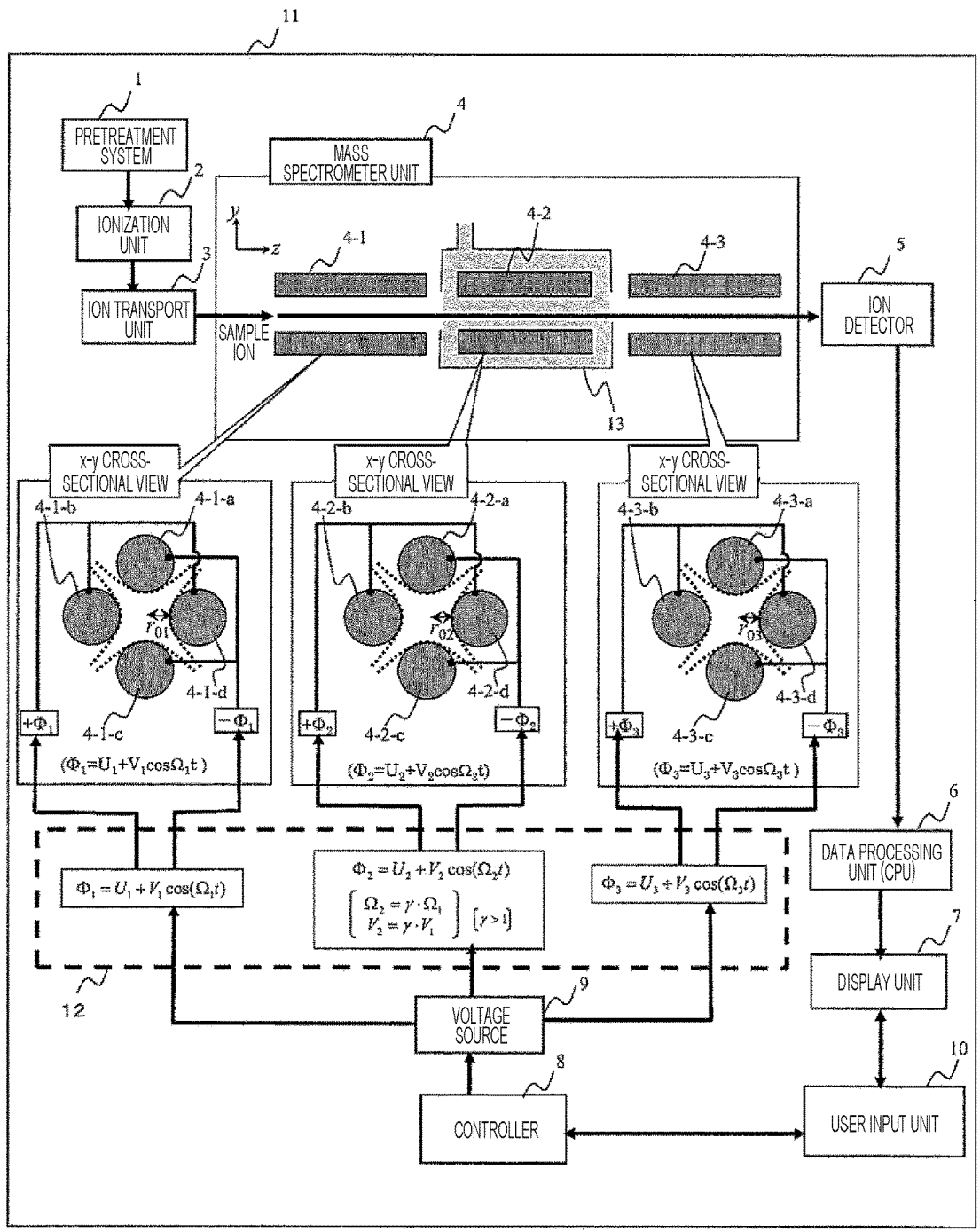
FIG. 1 is a schematic diagram of arrangement of various electrodes and a structure of a tandem type quadrupole mass spectrometry device of a first embodiment of the invention.
Figure 2:
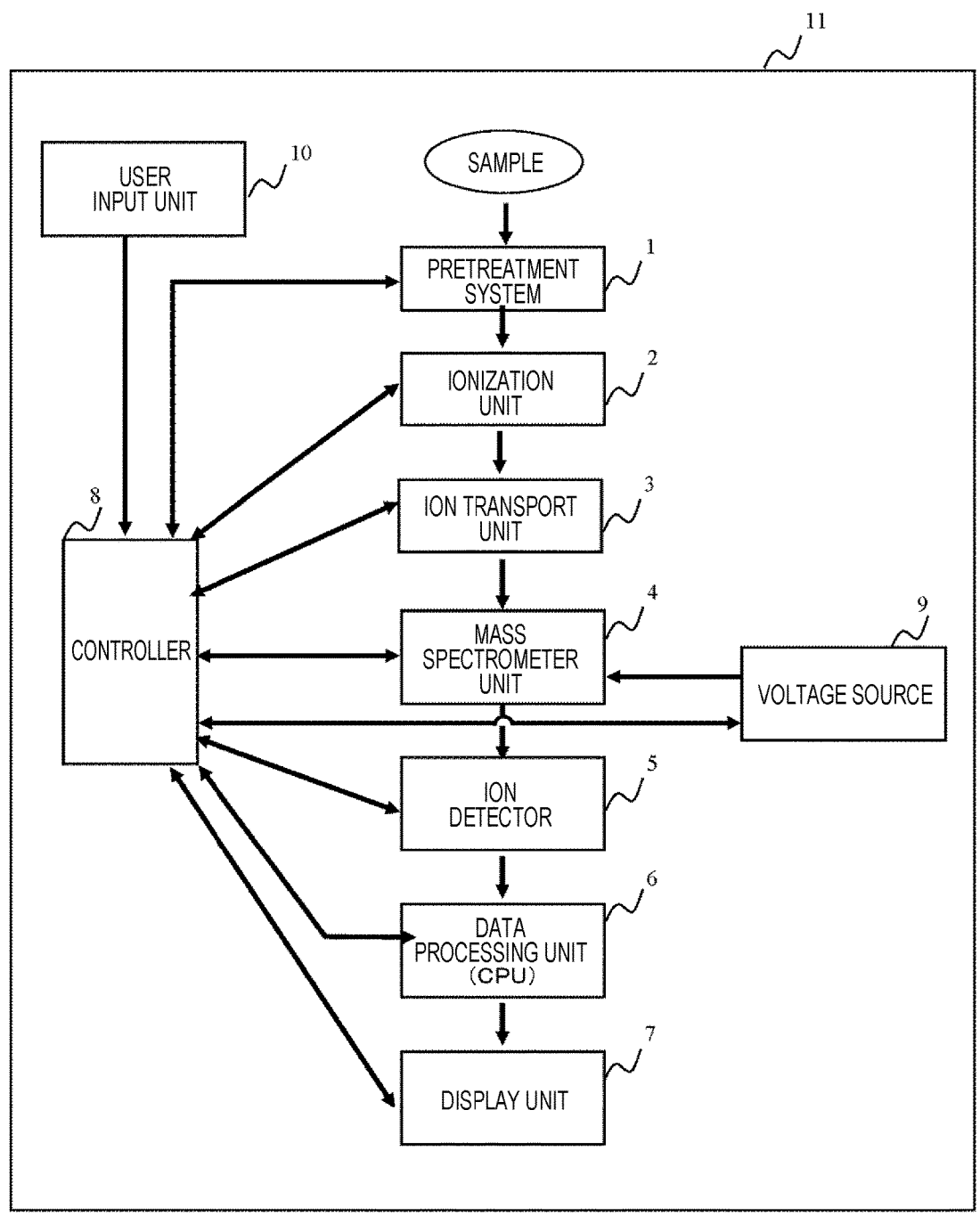
FIG. 2 is a schematic diagram of an entire mass spectrometry system for measuring mass spectrometry data according to the invention.

First, a first embodiment will be described with reference to FIG. 1 to FIG. 5b. FIG. 1 is a diagram illustrating a tandem type quadrupole mass spectrometry device including three stages of a QMS corresponding to a characteristic of the first embodiment, and FIG. 2 is a block diagram of an entire mass spectrometry system of the present embodiment. First, an analysis flow is shown for a mass spectrometry system 11. A sample to be mass-analyzed is separated and fractionated in terms of time in a pretreatment system 1 such as gas chromatography (GC) or liquid chromatography (LC), and sample ions successively ionized by an ionization unit 2 are injected into a mass spectrometer unit 4 through an ion transport unit 3 and mass-separated. Here, m is an ion mass and Z is a charge valence of an ion. A voltage to the mass separation unit 4 is applied from a voltage source 9 while being controlled by a controller 8. Finally, separated and passed ions are detected by an ion detector 5 and data-arranged/processed by a data processing unit 6, and mass spectrometry data corresponding to an analysis result thereof is displayed on a display unit 7. All this series of mass analysis processes (ionization of samples, transportation and incidence of a sample ion beam to the mass spectrometer unit 3, a mass separation process, ion detection, data processing, and command processing of a user input unit 10) are controlled by the controller 8. Here, as illustrated in FIG. 1, the mass separation unit 4 is configured by three rows of a quadrupole mass spectrometers (QMS) including four rod-like electrodes substantially coaxially connected to one another. Here, a multi-pole mass spectrometer including four or more rod-like electrodes may be used. In addition, as illustrated in FIG. 1, when a longitudinal direction of the rod-like electrodes is set to a z direction, and a sectional direction thereof is set to x and y planes, the four rod-like electrodes may correspond to cylindrical electrodes as illustrated in x-y cross sectional views of the rod-like electrodes or correspond to rod-like electrodes having a bipolar surface shape indicated by a dotted line.

In four electrodes of an ith stage of the QMS in the mass spectrometer unit 4, when electrodes facing each other are regarded as one set, a composite voltage of a direct current voltage and a high frequency voltage: $+(U_i+Vi \cos \Omega_i t)$ is applied to electrodes 4-*i*-*a* and 4-*i*-*c*, and an opposite phase voltage thereof: $-(U_i+Vi \cos \Omega_i t)$ is applied to electrodes 4-*i*-*b* and 4-*i*-*d*. Further, high frequency electric fields $E_{xi}$ and $E_{yi}$ shown in Equation (8) are generated among the four rod-like electrodes.

[Equation 8]

$$E_{x_i} = -\frac{\partial \Phi_i}{\partial x} = -\frac{2(U_i + V_i \cos \Omega_i t)}{r_{0_i}^2} \cdot x,$$
$$E_{y_i} = -\frac{\partial \Phi_i}{\partial y} = +\frac{2(U_i + V_i \cos \Omega_i t)}{r_{0_i}^2} \cdot y \quad (8)$$

Here, i denotes an ordinal number in stages of the QMS. In this case, i=1 to 3 since the QMS has three stages. Ionized sample ions are introduced along a central axis (z direction) between the rod-like electrodes and pass through the high frequency electric field of Equation (8). Stability of the ion trajectory in x and y directions at this time is determined based on non-dimensional parameters $a_i$ and $q_i$ below derived from an equation of motion (Mathieu equation) of ions between the rod-like electrodes.

[Equation 9]

$$a_i = \frac{8eZU_i}{\Omega_i^2 m r_{0_i}^2} \quad (9)$$

[Equation 10]

$$q_i = \frac{4eZV_i}{\Omega_i^2 m r_{0_i}^2} \quad (10)$$

Here, the non-dimensional parameters $a_i$ and $q_i$ correspond to stability parameters in the ith stage of the QMS. In addition, in Equations (9) and (10), $r_0$ denotes a half value of a distance between rod-like electrodes facing each other, e denotes an elementary charge, m/Z denotes a mass-to-charge ratio of an ion, U denotes a direct current voltage applied to the rod-like electrodes, and V and $\Omega$ denote an amplitude and an angular vibration frequency of a high frequency voltage. When values of $r_0$, U, V, and $\Omega$ are determined, respective ion species correspond to different points $(a_i, q_i)$ on an a-q plane of FIG. 3 depending on mass-to-charge ratios m/Z thereof. In this instance, from Equations (9) and (10), all the different points $(a_i, q_i)$ of the respective ion species are present on a straight line of the following Equation (11).

[Equation 11]

$$a_i = \frac{2U_i}{V_i} q_i \quad (11)$$

Figure 3:
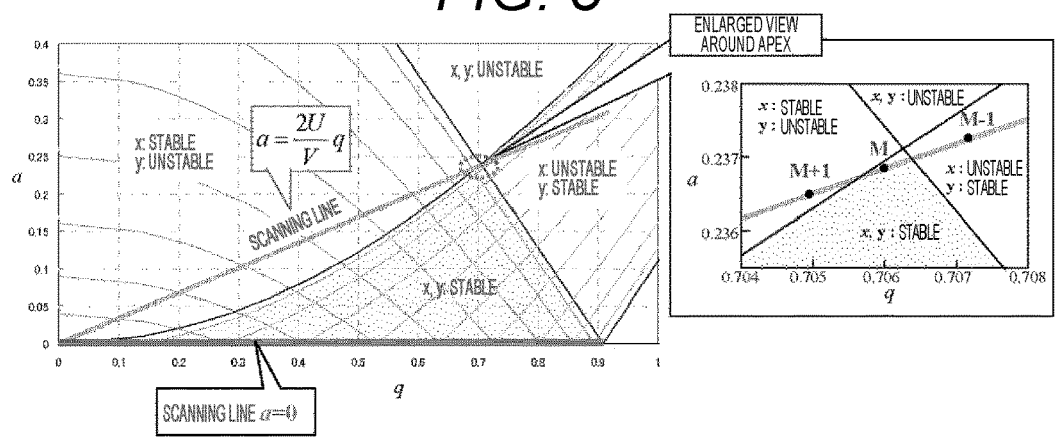
FIG. 3 is a diagram of an ion stable transmission area in a quadrupole electric field.
Figure 4A:
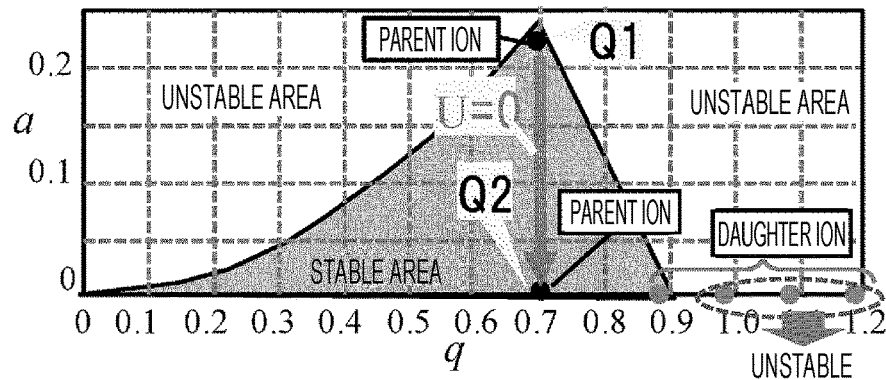
FIGS. 4A and 4B are conceptual diagrams of operating points in a first stage and a second stage of a QMS in a diagram of an ion stable transmission area of a quadrupole mass spectrometer.

FIG. 3 illustrates a quantitative range (stable transmission area) of $a_i$ and $q_i$ assigning a stable solution to ion trajectories in both the x and y directions. In order to allow only ion species having a specific mass-to-charge ratio m/Z to pass between the rod-like electrodes and cause unstable emission of the other ion species outside the QMS for mass separation, a U/V ratio needs to be adjusted to intersect a vicinity of an apex of the stable transmission area of FIG. 3 (FIG. 3). Stably transmitting ions pass between the rod-like electrodes in a z direction while vibrating. On the other hand, vibrations of destabilization ions diverge and the destabilization ions exit in the x and y directions. Using this point, in a tandem type quadrupole mass spectrometry system based on three stages of the QMS, in the first stage of the QMS (Q1), in order to pass only an ion species having a specific mass-to-charge ratio m/Z, a voltage applied to an electrode is adjusted such that an operating point corresponds to a point near the apex of the stable transmission area as illustrated in FIG. 4a. In the second stage of the QMS (Q2), a collision chamber 13 filled with a buffer gas such as a neutral gas is installed, and a specific ion species (parent ion) passing through Q1 is broken by collision induced dissociation, or the like to generate a dissociated ion (daughter ion) therein. In the third stage of the QMS (Q3), various daughter ions are subjected to mass spectrum analysis.

In the present embodiment, voltages applied to each ith stage of the QMS (the direct current voltage $U_i$ and the high frequency voltage $V_i \cos \Omega_i t$) are controlled as shown in control content 12 of FIG. 1. Referring to a voltage $U_1+V_1 \cos \Omega_1 t$ applied to Q1, in order to allow only a certain parent ion to pass by mass separation, $U_1$, $V_1$, and $\omega_1$ are adjusted such that the parent ion corresponds to the apex of the stable area based on Equations (8) and (9) as illustrated in FIG. 4b.

Figure 4B:
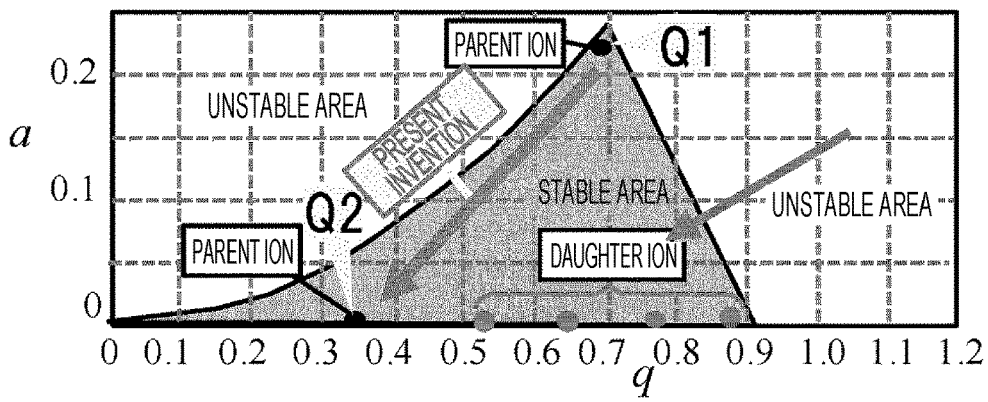
Figure 5A:
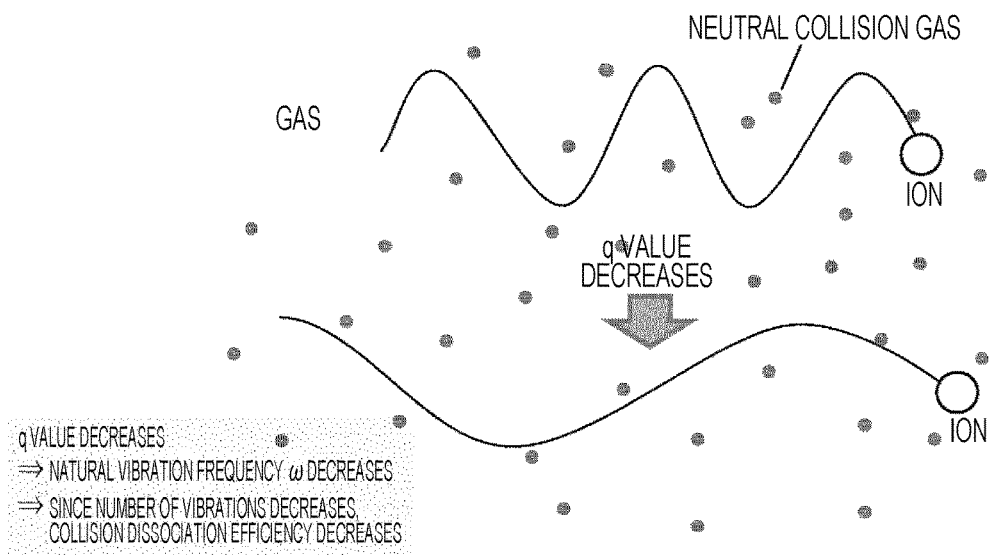
FIG. 5 is a FIGS. 5A and 5B are conceptual diagrams of a parent ion trajectory in the first stage and the second stage of the QMS.
Figure 5B:
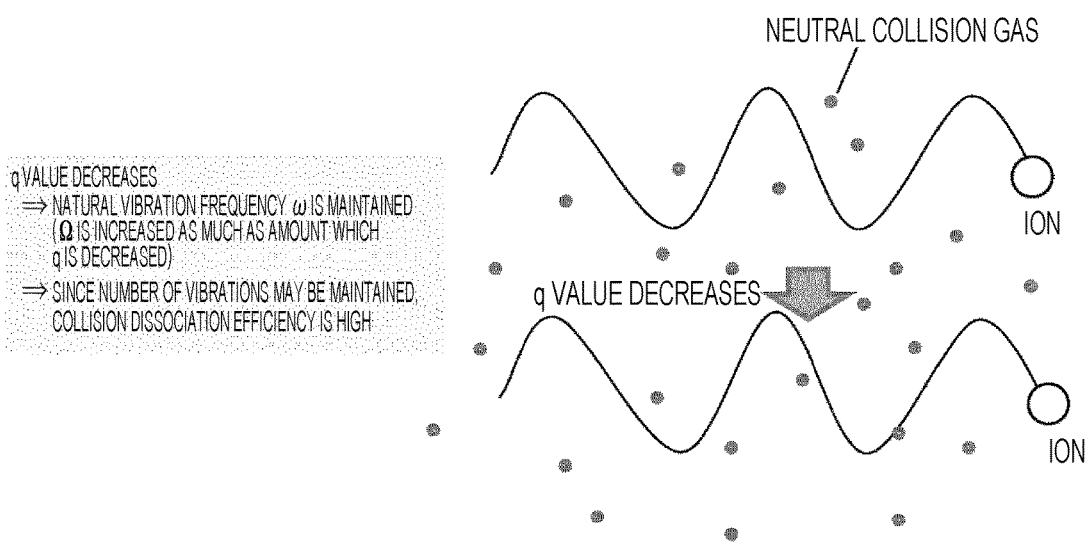

In Q2, as illustrated in FIG. 4b, the direct current voltage is set to $U_2=0$, and a control operation is performed based on Equation (7) such that the q value of the parent ion decreases when compared to the case of Q1 and a fundamental vibration frequency $\omega_2$ is substantially the same as that in the case of Q1 ($\omega_1$). However, in the present embodiment, since the half value $r_0$ of the distance between rod-like electrodes is the same among Q1, Q2, and Q3, a control operation is performed to obtain Equation (12).

[Equation 12]

$$\frac{V_1}{\Omega_1} = \frac{V_2}{\Omega_2} (\Omega_1 \neq \Omega_2) \quad (12)$$

That is, in order to set a value of V/$\Omega$ to be substantially the same between Q1 and Q2 and satisfy Equation (6),

[Equation 13]

$$V_2 = \gamma \cdot V_1 (\gamma > 1). \quad (13)$$

Further, an amplitude $V_2$ of a high frequency voltage $V_2 \cos \Omega 2t$ applied to Q2 and a value of an angular vibration frequency $\Omega_2$ are set and applied based on Equation (6) and Equation (13).

According to the present embodiment, effects that a mass number range of a daughter ion that may be stably transmitted is expanded, the number of vibrations of a parent ion is substantially the same as that in Q1, and generation efficiency of the daughter ion does not decrease are considered to be expectable merely by adjusting voltages applied to Q1 and Q2.

Figure 6:
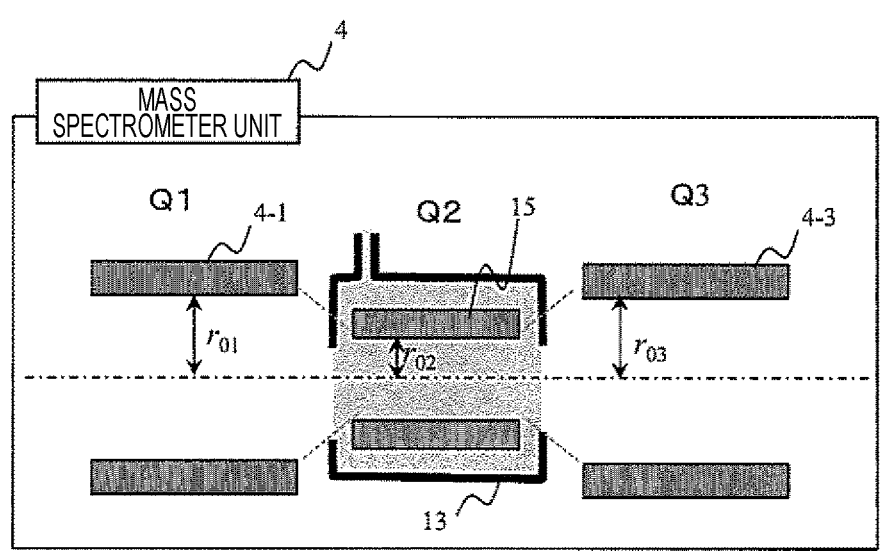
FIG. 6 is a diagram summarizing a result of deriving a potential distribution of generated potentials and an ion destabilization loss cumulative number by a simulation in the case of an ion guide and electrode arrangement/shape of a mass spectrometer unit according to a second embodiment of the invention.

Next, a second embodiment will be described with reference to FIGS. 6 and 7. Here, as illustrated in FIG. 6, in a rod-like electrode 15 of Q2, when a half value $r_{02}$ of a distance between rod-like electrodes has a relational expression below with respect to $r_{01}$ of Q1,

[Equation 14]

$$r_{0_2} = \frac{r_{0_1}}{\sqrt{\gamma}} (Y > 1) \quad (14)$$

Figure 7:
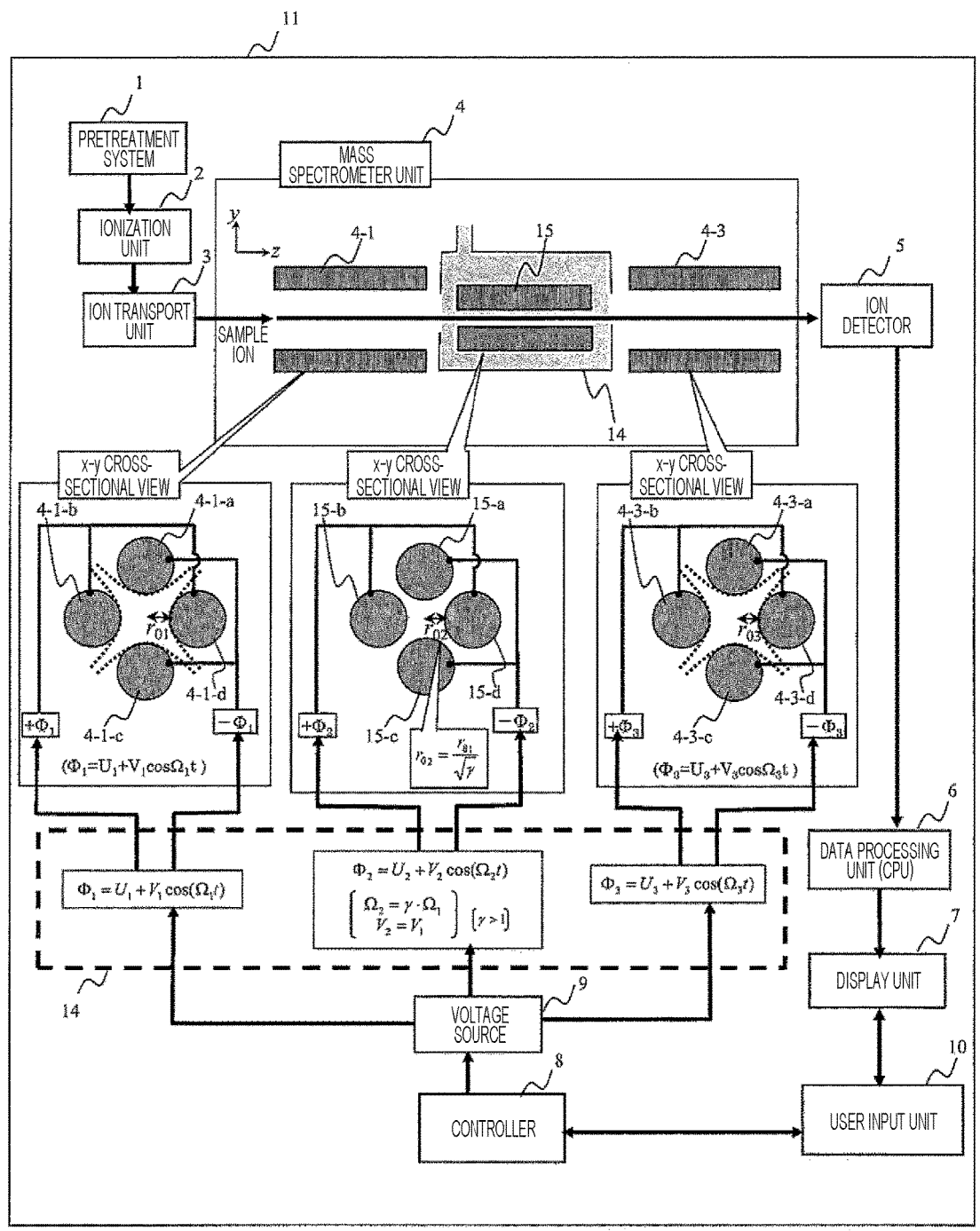
FIG. 7 is a schematic diagram of arrangement of various electrodes and a structure of a tandem type quadrupole mass spectrometry device in the second embodiment of the invention.

With regard to a voltage applied to the second stage of the QMS (high frequency voltage $V_2 \cos \Omega_{2t}$), as illustrated in control content 14 of FIG. 7,

[Equation 15]

$$V_2 = V_1 \quad (15)$$

A control operation is performed to satisfy Equation (6) and Equation (15). According to the present embodiment, since only an angular vibration frequency·2 of the high frequency voltage $V_2 \cos \Omega 2t$ of Q2 may be controlled, the same effect as that of the first embodiment is considered to be obtained by a relatively easy control operation.

Figure 8:
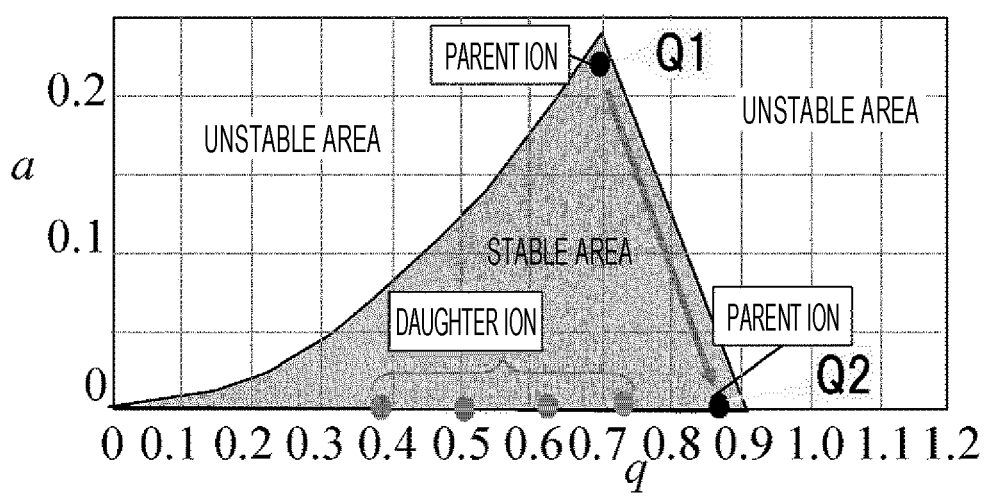
FIG. 8 is a conceptual diagram of an operating point in a first stage and a second stage of a QMS in an ion stable transmission area diagram of a quadrupole mass spectrometer according to a third embodiment of the invention.

Next, a third embodiment will be described with reference to FIG. 8. Here, a case where a parent ion is charged to be a multivalent ion (Z>1), and the like is presumed. In this case, a mass-to-charge ratio m/z of a daughter ion generated by dissociating the parent ion may not be smaller than a mass-to-charge ratio m/z of the parent ion. For example, when a parent ion of a mass number 5,000 [Da] is charged to be a pentavalent ion, a mass-to-charge ratio is m/z=1,000. When a monovalent daughter ion of a mass number 2,000 [Da] is generated, a mass-to-charge ratio becomes m/z=2,000 from the parent ion, and the mass-to-charge ratio increases. When such daughter ion generation is presumed, the $q_2$ value of the parent ion in Q2 is set to be larger than the $q_1$ value of the parent ion in the case of Q1 as illustrated in FIG. 8. In this case, an applied voltage or a distance between electrodes of Q2 may be controlled by substituting $\gamma<1$ into the control content 12 of FIGS. 1 and 7. According to the present embodiment, the same effect as that of the first and second embodiments is considered to be expectable even when the parent ion is a multivalent ion, and the daughter ion has a large mass-to-charge ratio.

Figure 9:
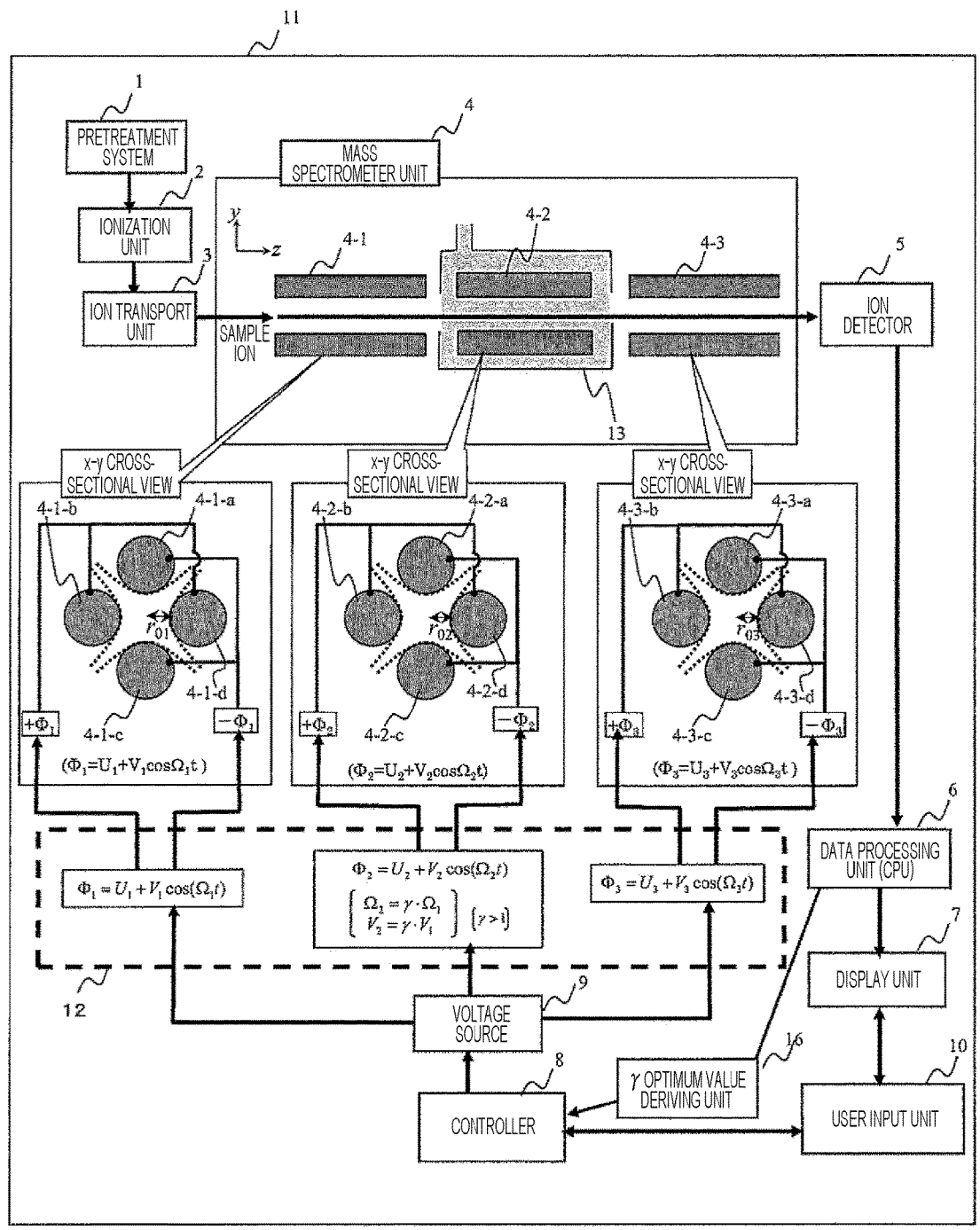
FIG. 9 is a schematic diagram of arrangement of various electrodes and a structure of a tandem type quadrupole mass spectrometry device.

Next, a fourth embodiment will be described with reference to FIG. 9. Here, based on mass spectrum data obtained by assigning a γ value corresponding to a control parameter within a certain range, an optimum value of the γ value is automatically derived and the applied voltage of Q2 is automatically corrected to an optimum γ value. According to the present embodiment, since an optimum value of γ is systematically derived and set without inputting an optimum γ value by the user, it is considered that highly accurate analysis may be easily performed.

REFERENCE SIGNS LIST

1 pretreatment system
2 ionization unit
3 ion transport unit
4 mass spectrometer unit
5 ion detector
6 data processing unit
7 display unit
8 controller
9 voltage source
10 user input unit
11 entire tandem type mass spectrometry system
12 applied voltage control content
13 collision chamber
14 applied voltage control content in second embodiment
15 electrode of Q2 in second embodiment
γ optimum value deriving unit

The invention claimed is:

1. A mass spectrometry device, comprising:
 a mass spectrometer unit which includes at least four rod-like electrodes, applies a direct current voltage U and a high frequency voltage $V \cos \Omega t$ to the rod-like electrodes to generate a multi-pole field greater than or equal to a quadrupole field of a high frequency between the rod-like electrodes, and mass-selects/separates an ion species having a specific mass-to-charge ratio m/z; and
 a detector which detects an ion passing through the mass spectrometer unit,
 wherein at least two or more stages of the mass spectrometer unit are coaxially provided in series, and
 the voltages applied to the rod-like electrodes are controlled and a half value $r_0$ of a distance between the rod-like electrodes of the mass spectrometer unit is changed in a first stage of the mass spectrometer unit and a second stage of the mass spectrometer unit such that a fundamental vibration frequency of a certain ion species is substantially the same between the first stage and the second stage.

2. The mass spectrometry device according to claim 1, wherein at least three stages of the mass spectrometer unit are included, an ion species having a certain mass-to-charge ratio is passed in a first stage of the mass spectrometer unit, a dissociated ion is generated by collision induced dissociation with respect to a certain ion passing through the first stage in a second stage of the mass spectrometer unit, and the dissociated ion is mass-analyzed in a third stage of the mass spectrometer unit.

3. The mass spectrometry device according to claim 1, wherein the voltages applied to the rod-like electrodes are controlled and the distance between the rod-like electrodes of the mass spectrometer unit is changed in the first stage of the mass spectrometer unit and the second stage of the mass spectrometer unit such that a value of $V/(r_0^2 \Omega)$ is substantially the same between the first stage and the second stage.

4. The mass spectrometry device according to claim 1, wherein the voltages applied to the rod-like electrodes of the mass spectrometer unit are controlled in the first stage of the mass spectrometer unit and the second stage of the mass spectrometer unit such that a value of a ratio $V/\Omega$) of an amplitude value V of the high frequency voltage to an angular vibration frequency $\Omega$ of the high frequency voltage is substantially the same between the first stage and the second stage.

5. The mass spectrometry device according to claim 1, wherein the voltages applied to the rod-like electrodes are controlled and the distance between the rod-like electrode of the mass spectrometer unit is changed such that a value of $V/(r_0^2 \Omega^2)$ in the second stage of the mass spectrometer unit is smaller than a value of $V/(r_0^2 \Omega^2)$ in the first stage of the mass spectrometer unit by γ times with respect to the high frequency voltage $V \cos \Omega t$ applied to the rod-like electrodes and the half value $r_0$ of the distance between the rod-like electrodes.

6. The mass spectrometry device according to claim 5, wherein an optimum γ value from which an optimum analysis result is obtained is automatically derived by assigning the γ value within a certain range.

7. The mass spectrometry device according to claim 1, wherein the voltages applied to the rod-like electrodes are controlled and a distance between the rod-like electrode of the mass spectrometer unit is changed such that a value of $V/(r_0^2\Omega^2)$ in the second stage of the mass spectrometer unit is larger than a value of $V/(r_0^2\Omega^2)$ in the first stage of the mass spectrometer unit by $\gamma$ times with respect to the high frequency voltage $V \cos \Omega t$ applied to the rod-like electrodes and the half value $r_0$ of the distance between the rod-like electrodes.

8. The mass spectrometry device according to claim 1, wherein the voltages applied to the rod-like electrodes of the mass spectrometer unit are controlled such that a value $\Omega$ in the second stage of the mass spectrometer unit is larger than a value $\Omega$ in the first stage of the mass spectrometer unit by $\gamma$ times with respect to the high frequency voltage $V \cos \Omega t$ applied to the rod-like electrodes.

9. The mass spectrometry device according to claim 1, wherein the voltages applied to the rod-like electrodes of the mass spectrometer unit are controlled such that a value $\Omega$ in the second stage of the mass spectrometer unit is smaller than a value $\Omega$ in the first stage of the mass spectrometer unit by $\gamma$ times with respect to the high frequency voltage $V \cos \Omega t$ applied to the rod-like electrodes.

10. A mass spectrometry device, comprising:
a mass spectrometer unit which includes at least four rod-like electrodes, applies a direct current voltage U and a high frequency voltage $V \cos \Omega t$ to the rod-like electrodes to generate a multi-pole field greater than or equal to a quadrupole field of a high frequency between the rod-like electrodes, and mass-selects/separates an ion species having a specific mass-to-charge ratio m/z; and
a detector which detects an ion passing through the mass spectrometer unit,
wherein at least two or more stages of the mass spectrometer unit are coaxially provided in series, and
a stability parameter of a first stage of the mass spectrometer unit is set to be $\gamma$ times ($\gamma>1$) a stability parameter of a second stage of the mass spectrometer unit, and an angular vibration frequency $\Omega_1$ of the first stage of the mass spectrometer unit and an angular vibration frequency $\Omega_2$ of the second stage of the mass spectrometer unit are set to satisfy a following relation:

$$\Omega_2 = \Omega_1 \cdot \gamma', \quad 1 < \gamma' \leq \gamma,$$

(stability parameter)$=4eZV/\Omega^2 mr_0^2$, where $r_0$ denotes a half value of a distance between rod-like electrodes facing each other, e denotes an elementary charge, V denotes an amplitude of a high frequency voltage, and $\Omega$ denotes an angular vibration frequency.

11. The mass spectrometry device according to claim 10, wherein the stability parameter is set by changing the distance between the rod-like electrodes.

12. The mass spectrometry device according to claim 10, wherein the stability parameter is set by controlling voltages applied to the rod-like electrodes.

* * * * *